(12) United States Patent
Harrington

(10) Patent No.: US 8,764,799 B2
(45) Date of Patent: Jul. 1, 2014

(54) DEVICE AND METHOD FOR NASAL SURGERY

(76) Inventor: Douglas C. Harrington, Los Altos Hills, CA (US)

( * ) Notice: Subject to any disclaimer, the term of this patent is extended or adjusted under 35 U.S.C. 154(b) by 205 days.

(21) Appl. No.: 13/484,650

(22) Filed: May 31, 2012

(65) Prior Publication Data

US 2012/0310280 A1    Dec. 6, 2012

Related U.S. Application Data

(60) Provisional application No. 61/491,448, filed on May 31, 2011.

(51) Int. Cl.
*A61B 17/04*   (2006.01)
(52) U.S. Cl.
USPC ............................................. 606/232; 606/196

(58) Field of Classification Search
USPC .......... 128/897, 898; 606/139, 144, 145, 148, 606/149, 150, 196, 228, 229, 230, 231, 232
See application file for complete search history.

(56) References Cited

U.S. PATENT DOCUMENTS

| 4,938,234 | A | * | 7/1990 | Capriotti | 128/898 |
|---|---|---|---|---|---|
| 5,713,839 | A | * | 2/1998 | Shea | 602/17 |
| 7,419,497 | B2 | * | 9/2008 | Muni et al. | 606/196 |
| 7,785,315 | B1 | * | 8/2010 | Muni et al. | 604/510 |
| 8,038,712 | B2 | * | 10/2011 | van der Burg et al. | 623/10 |
| 8,133,276 | B2 | * | 3/2012 | Saidi | 623/10 |
| 2003/0018377 | A1 | * | 1/2003 | Berg et al. | 623/1.11 |
| 2005/0251143 | A1 | * | 11/2005 | Dillard | 606/72 |
| 2007/0129751 | A1 | * | 6/2007 | Muni et al. | 606/196 |
| 2009/0312792 | A1 | * | 12/2009 | Fallin et al. | 606/228 |

* cited by examiner

*Primary Examiner* — Ryan Severson
*Assistant Examiner* — Jonathan W Miles
(74) *Attorney, Agent, or Firm* — K. David Crockett, Esq.; Niky Economy Syrengelas, Esq.; Crockett & Crockett, PC

(57) ABSTRACT

Methods, devices and systems for the treatment of nasal valve collapse or other conditions of the ear, nose or throat.

7 Claims, 10 Drawing Sheets

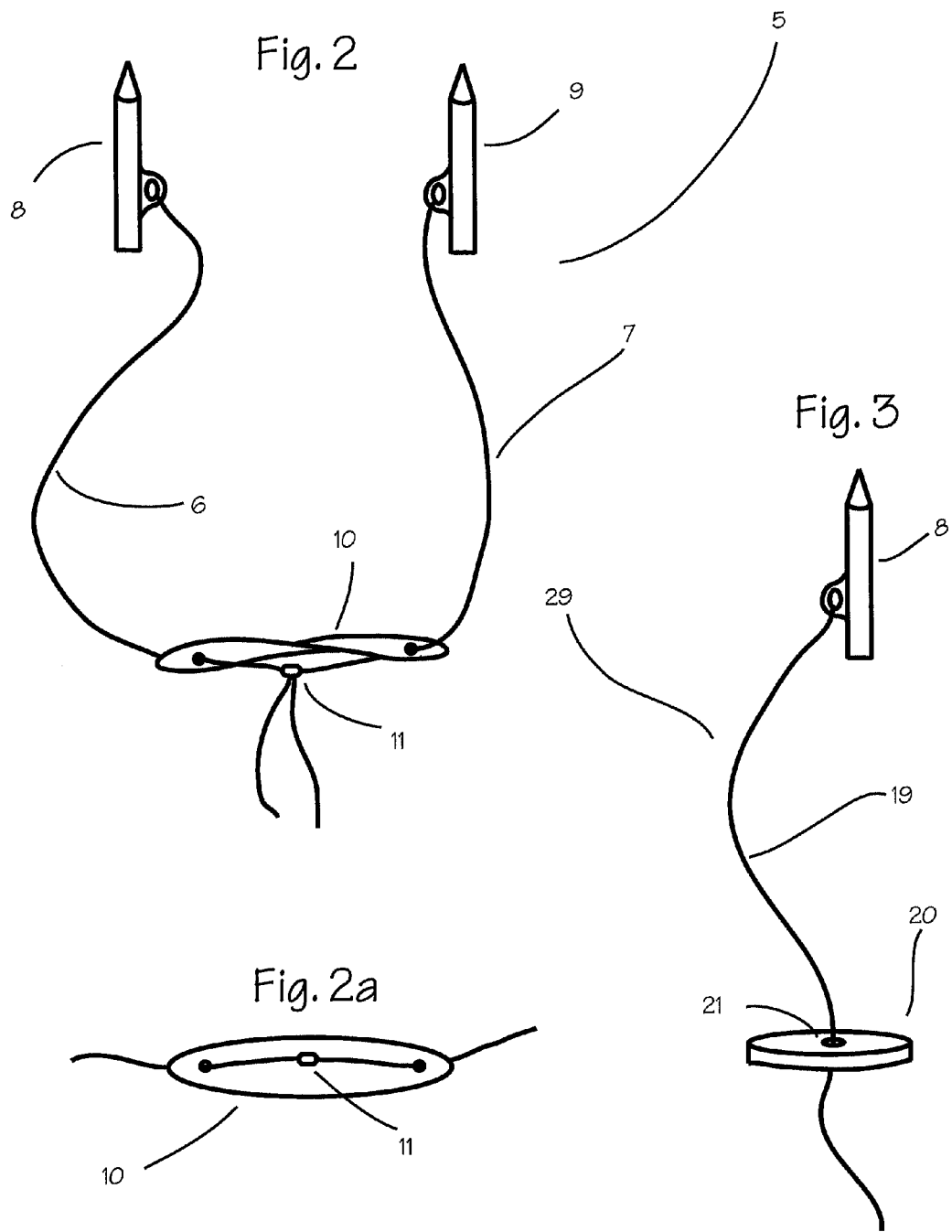

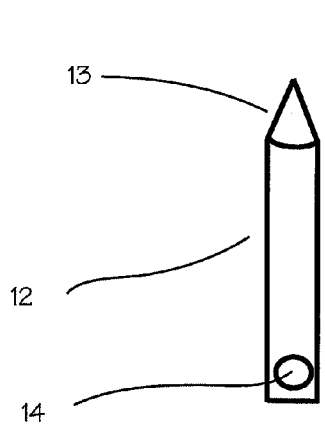
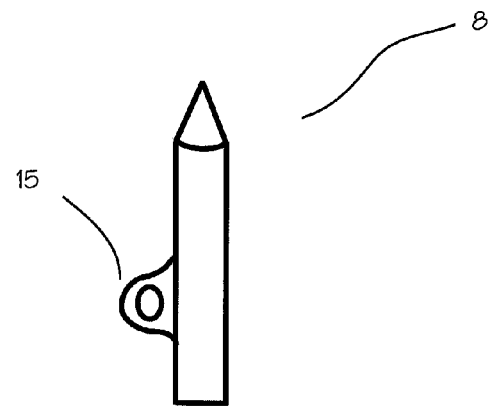
FIG. 4a    FIG. 4b
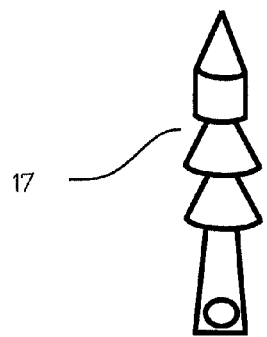
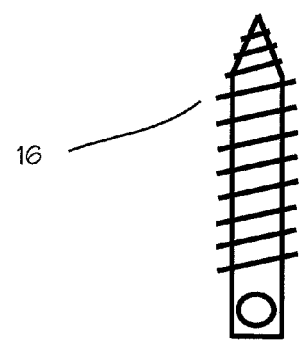
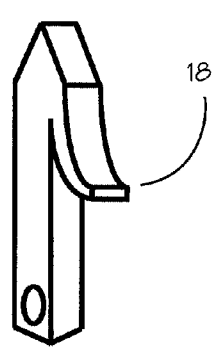
FIG. 4c    FIG. 4d    FIG. 4e

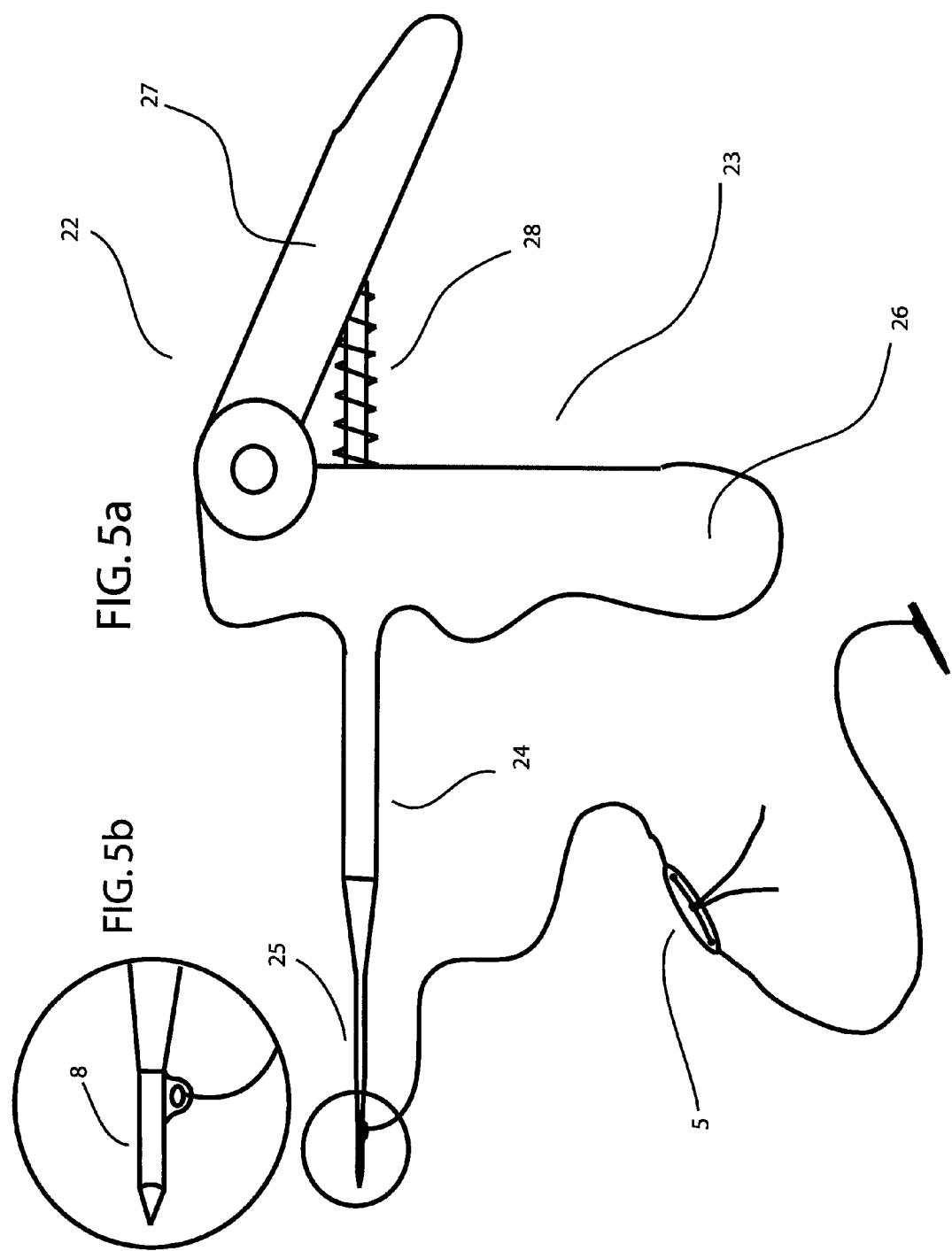

3

DEVICE AND METHOD FOR NASAL SURGERY

This application claims priority to U.S. Provisional Patent App. 61/491,448 filed May 31, 2011.

FIELD OF THE INVENTION

The inventions described below relate to the field of methods, devices and systems for the treatment of nasal valve collapse or other conditions of the ear, nose or throat.

BACKGROUND OF THE INVENTIONS

One common cause of nasal airway obstruction is collapse of the internal nasal valve. Nasal valve collapse is a condition where the sidewalls of your nostrils collapse as you breathe in. It can occur by itself, or along with other reasons that cause nasal congestion. For example, it may occur years after rhinoplasty due to weakening of the cartilages that supports the side of the nostrils and other times it happens without any surgery or trauma.

Support of the nasal valve is currently achieved by several different treatment methods. However, all of these methods have drawbacks such as being expensive, unsightly, uncomfortable to wear and remove the nasal support and may cause skin irritation. Other procedures result in sequelae from the incisions and tissue harvesting has been reported. These procedures may also leave undesirable scars on the nose and ears and cannot be performed within an office setting.

Thus, there is a need to provide a device, system and method for correction of collapse of a nasal valve that is inexpensive, can be performed within an office setting and does not require incision within the face of the patient.

SUMMARY

Nasal implants for opening or supporting the internal and external nasal valves of the nasal cavity are provided. The implant may include a loop of suture with two suture anchors attached. The suture is looped through the nasal valve and the attached anchors are placed in juxtaposition to the facial bone. The implant includes a supporter or hammock at the location of the suture looping through the nasal valve. Another implant includes one length of suture with one anchor attached at the distal end and one button like supporter attached at the proximal end. The anchor is attached to the facial bone and the supporter is placed within the nasal valve tissues.

Devices and systems to deliver implants and attach anchors to the bone or facial tissues are also provided. They may be delivered and attached via a handle like system or inserter with an anchor receiving receptacle at the distal end. An anchor is attached to the distal end and a device is used to puncture and traverse tissue with an anchor tip to a targeted location. The device is then activated to deliver the anchor to bone or tissue and release the anchor into the bone or tissue.

In addition, methods to perform nasal surgery are provided wherein delivery of the implant is through the internal nasal wall and adjacent tissues to attach a fixation device using only a trans-nasal or endo-nasal approach. Alternatively, delivery of the implant may be performed by employing both a trans-nasal and trans-oral approach to deliver and attach an implant. The method offers the advantage that a transconjuctival or facial incision is avoided in the treatment of nasal valve collapse.

BRIEF DESCRIPTION OF THE DRAWINGS

FIG. 2 is side view of a sling device;
FIG. 2a is a bottom view of the sling device as shown in FIG. 2;
FIG. 3 is side view of a single suture batten device;
FIGS. 4a through 4e are representative shapes and designs for the anchors for the devices;
FIG. 5a is a side view of a delivery system for the device;
FIG. 5b is a close up view of the distal tip of the delivery system in FIG. 5a.

DETAILED DESCRIPTION OF THE INVENTIONS

Figure 1:
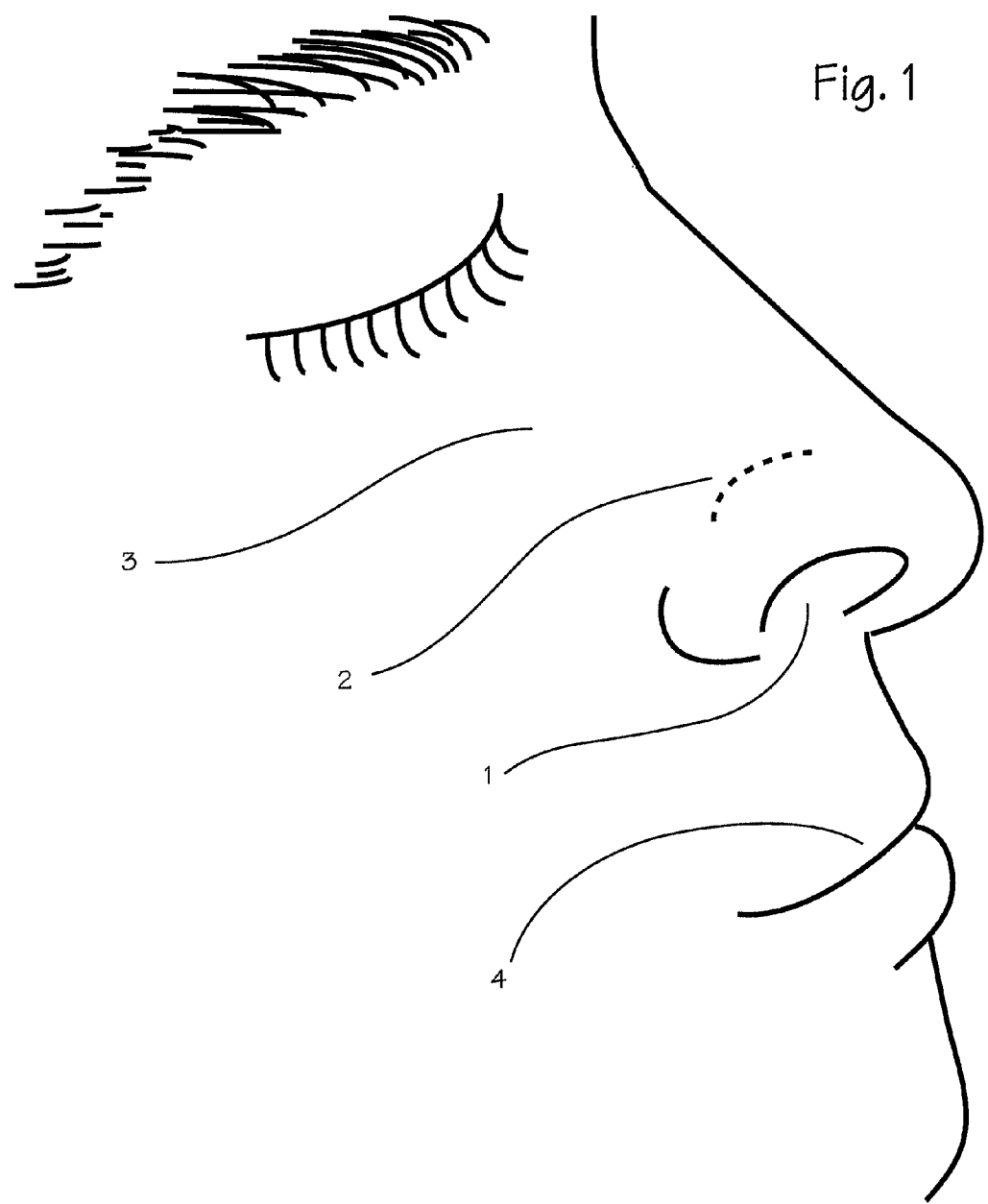
FIG. 1 is a right lateral view of the face and nose.

FIG. 1 illustrates a right lateral side view of a human face. Nasal features include the nasal opening or nostril 1 that leads into the nasal cavity where the internal nasal valve 2 shown in phantom is located. The facial bone making up part of the skull underlying facial tissues, lateral superior to the nose, is the maxilla 3. The opening to the mouth or oral fissure 4 is located below the nostrils.

FIG. 2 illustrates a suture sling 5. The device includes sutures 6 and 7 permanently attached to two suture anchors 8 and 9. Located at the bottom end of the sling is supporter or hammock 10 with the suture threaded through the supporter from the bottom. Connecting the two ends of the suture directly below the supporter is a slipknot 11 (or running knot) that allows tightening and loosening of the device. FIG. 2a is a bottom view of the supporter 10 with suture threaded through the supporter with a slipknot 11.

The sutures link and create tension between the nasal tissues and facial bone by coupling the bone anchors to the supporter or hammock 10. Sutures 6 and 7 can be made from any of commercially available suture materials such as silk, nylon, polyester and polypropylene and can include monofilaments or braided types. Suture thickness can range from 0.01 mm (#11-0) to 0.80 mm (#6) with a range of 0.07 mm (#6-0) to 0.50 mm (#2) preferred. Tape or rectangular cross-sectional shaped suture can also be used to better support tissue under tension. In certain instances, it may be desirable to have the suture material act more like a spring and consist of a greater level of flexibility and recoverable elongation. Materials suitable for this characteristic include silicone rubbers, fluoroelastomers, polyether block amides (Pebax™) and various other thermoplastic elastomers. Various other materials can be used as a tether depending upon the specific mechanic/physical/physiological properties desired. For example, poly-paraphenylene terephthalamide (Kevlar™), aromatic polyester (Vectran™), ultra-high-molecular-weight polyethylene (Spectra™), have superior mechanical strengths to the suture material previously mentioned. Felts, woven sheets, braided materials and composites may also be suitable for this component.

The supporter 10 prevents loss of nasal valve suspension and tissue collapse overtime. This is achieved by more widely distributing tension along the bottom portion of the supporter positioned within the nasal valve tissues which in turn, prevents suture migration and/or extrusion while under tension.

The supporter 10 can be placed within the tissues of the nose at the area of collapse. Typically, the internal nasal valve is the area of collapse so the supporter will be placed underneath the endonasal mucosa at the internal nasal valve. The supporter is placed between the nasal mucosa and the lateral nasal wall cartilages, specifically at the junction of the caudal edge of the upper lateral cartilage and the cephalic edge of the lower lateral cartilage. The supporter can be several different shapes and sizes and can be solid, porous, sintered, woven, braided and the like. In FIGS. 2 and 2a the supporter is shaped as a flat oval sheet. Shapes can include but are not limited to round, rectangular, diamond and the like. Thickness can range from 0.01 mm to several millimeters and dimensions of the oval can range from several millimeters to several centimeters with approximately 0.5 cm by 1 cm preferred.

The supporter 10 can be solid or of a porous design to better integrate the device into the tissues by allowing tissue ingrowth after implantation. The supporter can include an open pore design on the surface or a particular depth or throughout the entire component depending upon physiological response desired and limitations of the component material and manufacture. Porous designs include flexible materials such as polyester (Dacron™), expanded polytetrafluoroethylene (Gortex™) and porous silicone. More rigid porous materials such as sintered polyethylene (Porex™) may be employed depending upon mechanical properties desired.

FIG. 4a through 4e illustrate various shapes of the suture anchors 8. These anchors attach soft tissue to bone and can include screws, staples, tacks and the like. The anchor 12 which is inserted into the bone with distal point 13 first, contains an eyelet which is a hole 14 or a loop 15 through which the suture passes or is attached to anchor. The suture can also be attached to the anchor by various other methods including crimping suture end into a proximal blind hole of anchor and gluing. Flanges can also be positioned along the length of the anchor to prevent over insertion into the bone.

The anchors can be tacked in with or without a predrilled hole. Screws as shown in FIG. 4d can have various thread 16 designs including straight threads for pre-drilled holes and bone self tapping threads for attachment without pre-drilled holes. Anchors can also have features such as barbs 17 or cantilevers 18 which provide an impedance to anchor pull out. Materials used to manufacture anchors include titanium, coated titanium or stainless steel. Bioresorbable or bioabsorbable anchors may also be employed if eventual resorption and replacement of the anchor by the host bone is preferred. Bioresorbable materials include hydroxylapatite (HA), polyglycolic acid, polyglactin, polydioxone and polyglyconate.

FIG. 3 illustrates a device having a single suture 29. This device includes one suture 19 with one anchor attached to the distal end and one button like supporter 20 attached at the proximal end. Mechanically, the device functions similarly to a single rope disk swing or tree swing. Tension and support of the nasal wall is created when the suture anchor is attached to the facial bone and the supporter is placed within the nasal tissues and the suture is tensioned to open the nasal passage.

The suture passes through a hole 21 in the supporter and is tightened with a slipknot below (not shown). The anchor and suture can be manufactured with similar designs and materials used in the suture sling design shown in FIG. 2. The supporter can be manufactured with similar designs and materials as the supporter used in the suture sling design of FIG. 2, but may need to be stiffer to create enough support and prevent suspension loss overtime.

The suture anchor can be delivered and attached to the bone with an inserter 22 as shown in FIG. 5. The inserter includes a handle 23 and elongated member 24 attached to handle. Also shown in FIG. 5 is a suture sling 5 temporarily attached to distal end portion 25 of elongated member 24 of the inserter. FIG. 5a shows a close up view of an anchor attached to the distal end portion of inserter. Attachment can include a receptacle component at distal end of inserter to releasably receive proximal end of anchor device.

The inserter attachment of anchor to bone can be accomplished in any of the commercially know ways to attach suture anchors for orthopedic and arthroscopic procedures. Alternatively, the attachment can be made using a spring like manual staple gun mechanism. As the two handle components 26 and 27 are squeezed together, potential energy is stored in a spring 28. At a critical point during spring compression, the energy from the spring is released to a piston in contact with the proximal end of the anchor. The piston's impact on the anchor drives the anchor into the bone.

Figure 6:
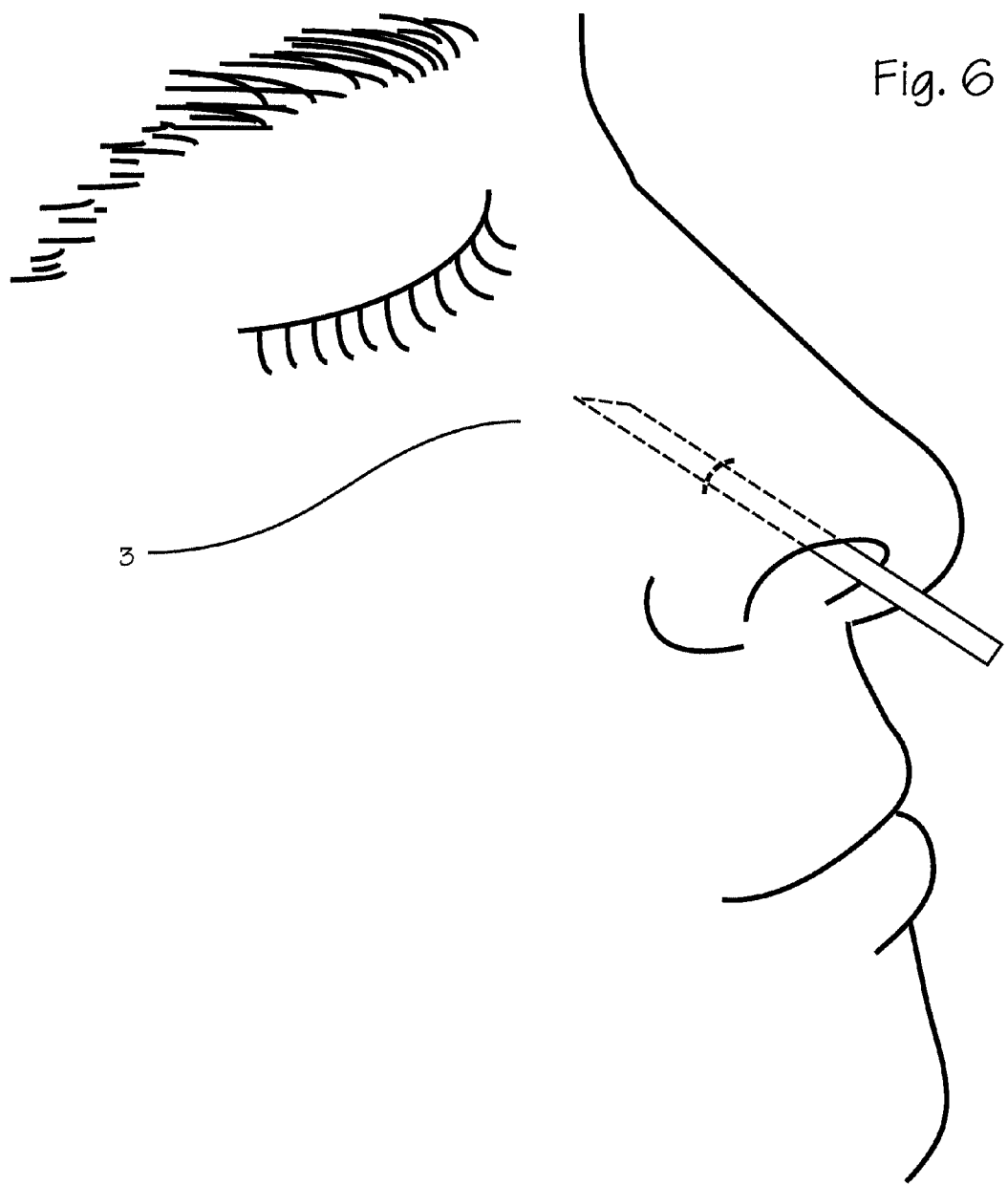
FIGS. 6 through 11 illustrate the steps for performing the method for treatment of nasal collapse.
Figure 7:
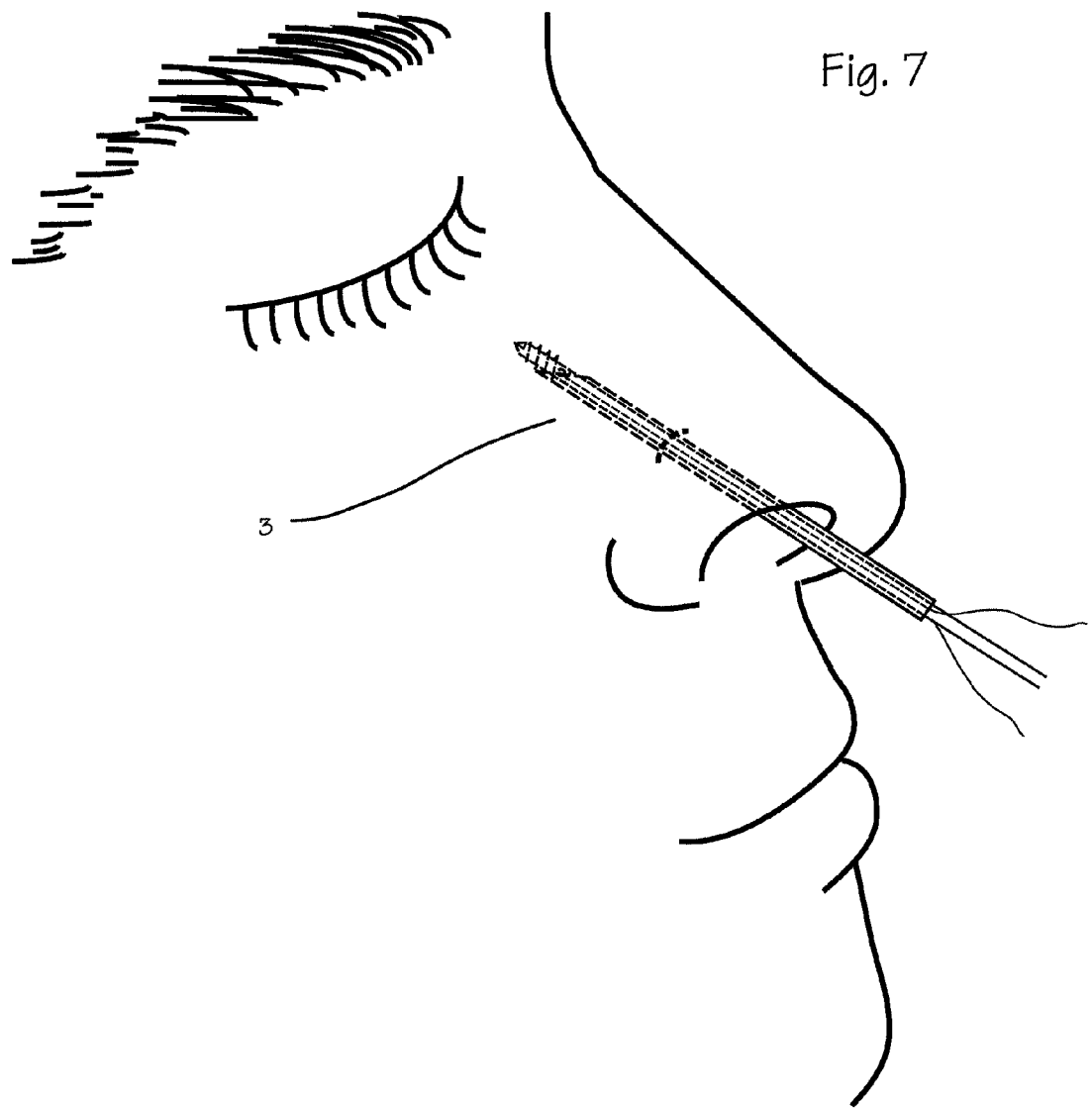

FIGS. 6 through 11 illustrate the device as used. In use, a patient is prepared for the minimally invasive trans-nasal rocedure. The procedure may be accomplished within an office setting. FIG. 6 illustrates that a hypodermic needle is used to trans-nasally puncture and create a tunnel to the nasal mucosa near or at the area of collapse. The needle is advanced with a stylet or obturator into the facial tissue up to the targeted bone fixation location. FIG. 6 illustrates the needle in position once the stylet is removed. A first suture anchor 8 is attached to the distal end of the inserter 25, and the suture anchor 8 is then advanced into the facial tissue. FIG. 7 illustrates a self-tapping bone screw with 2 attached trailing sutures and a driver. The suture anchor is driven through the trans-nasal puncture or tunnel either manually or with a power driver. The needle is then withdrawn so that the anchor with the trailing suture and driver remain. Advancement is achieved through a trans-nasal puncture of the nasal mucosa near or at an area of collapse and up to the targeted bone fixation location within the maxilla bone. The inserter, with anchor attached as shown in FIGS. 5a and 5b, is trans-nasally advanced to nasal mucosa of a collapsed portion of nasal wall. The distal tip of anchor then punctures the nasal mucosa at or near the area of collapse and passes into the facial tissue to the targeted location of facial bone attachment. The physician activates the handle of the inserter to permanently attach the bone anchor to bone and release the anchor from distal tip of the inserter.

Figure 8:
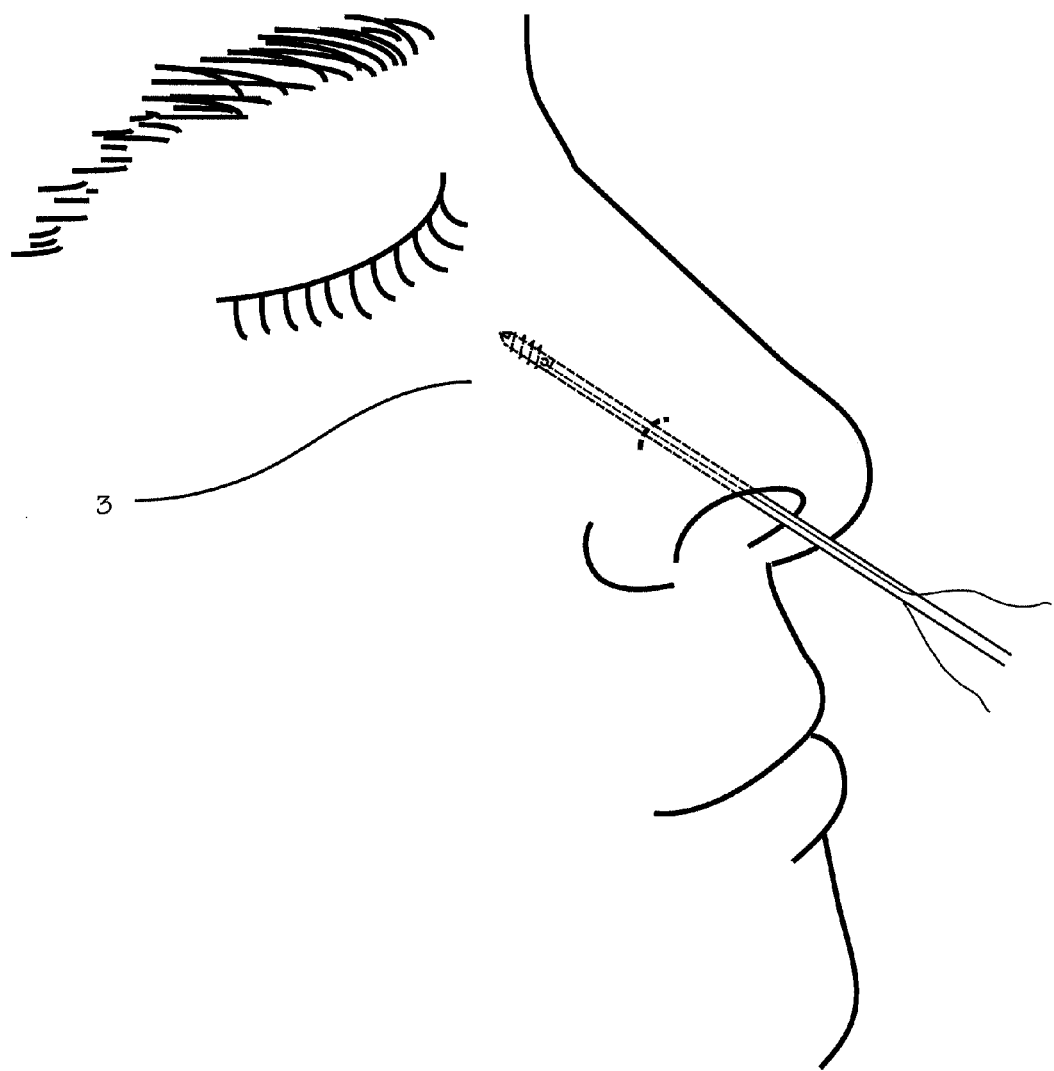
Figure 9:
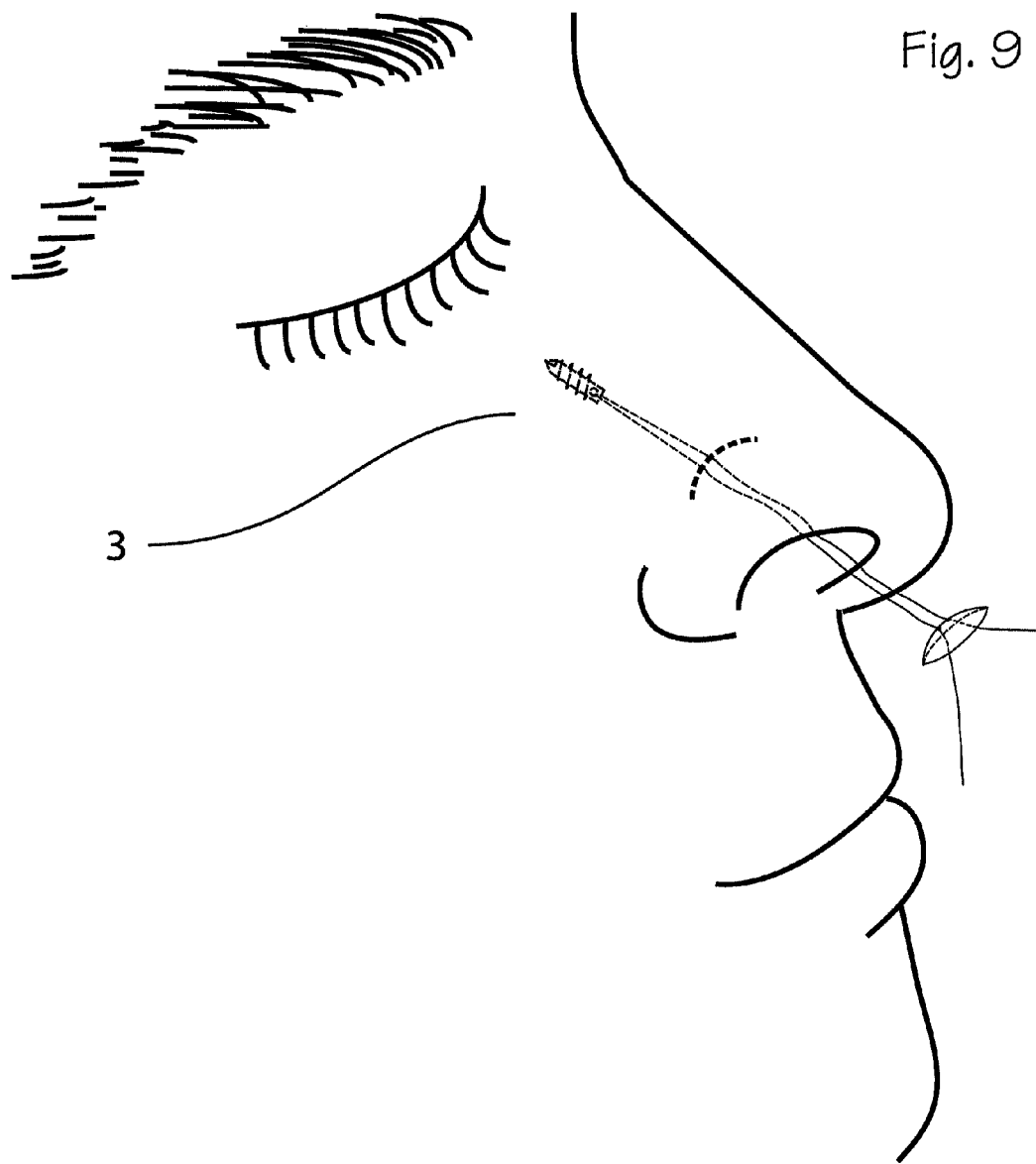
Figure 10:
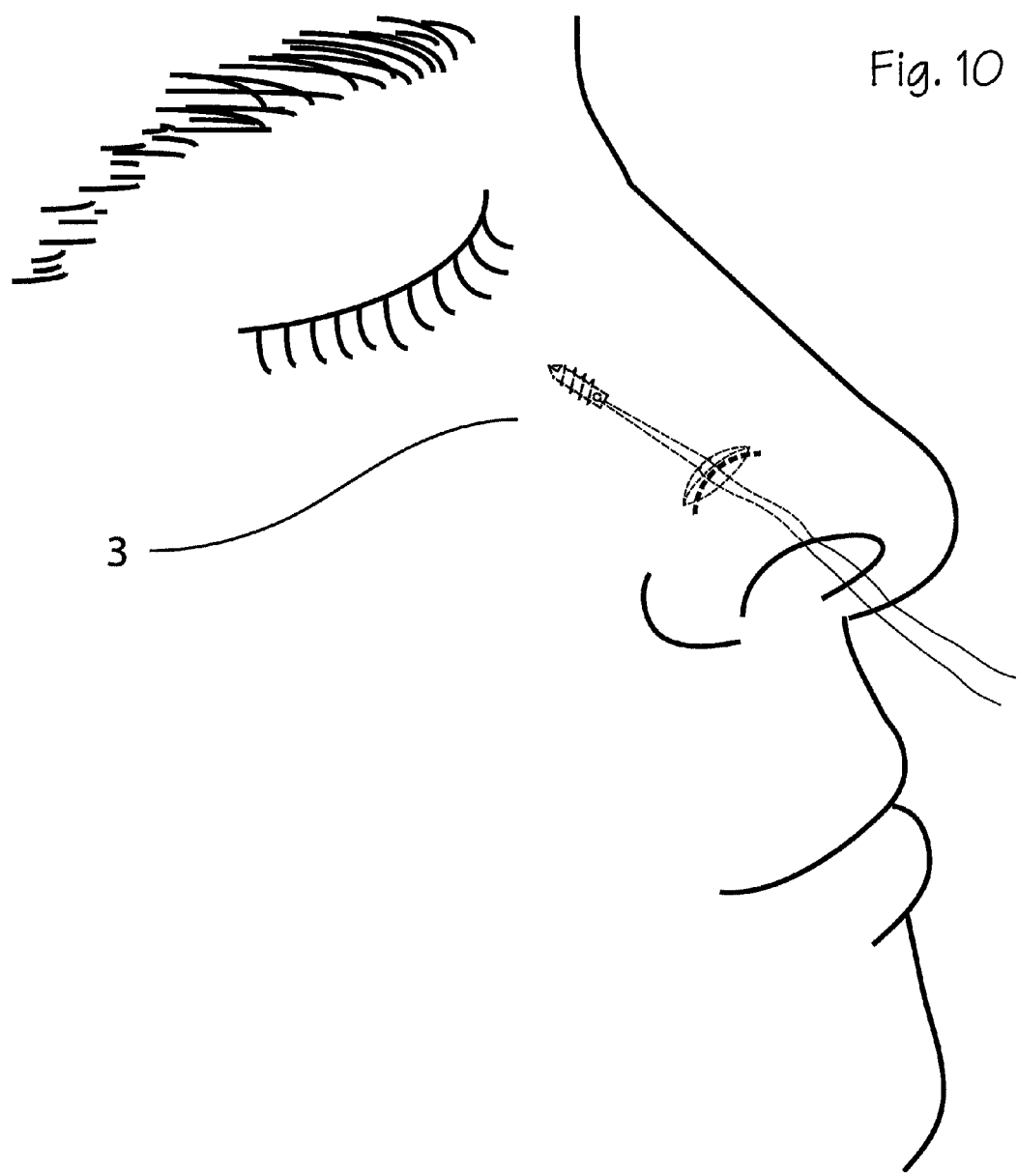
Figure 11:
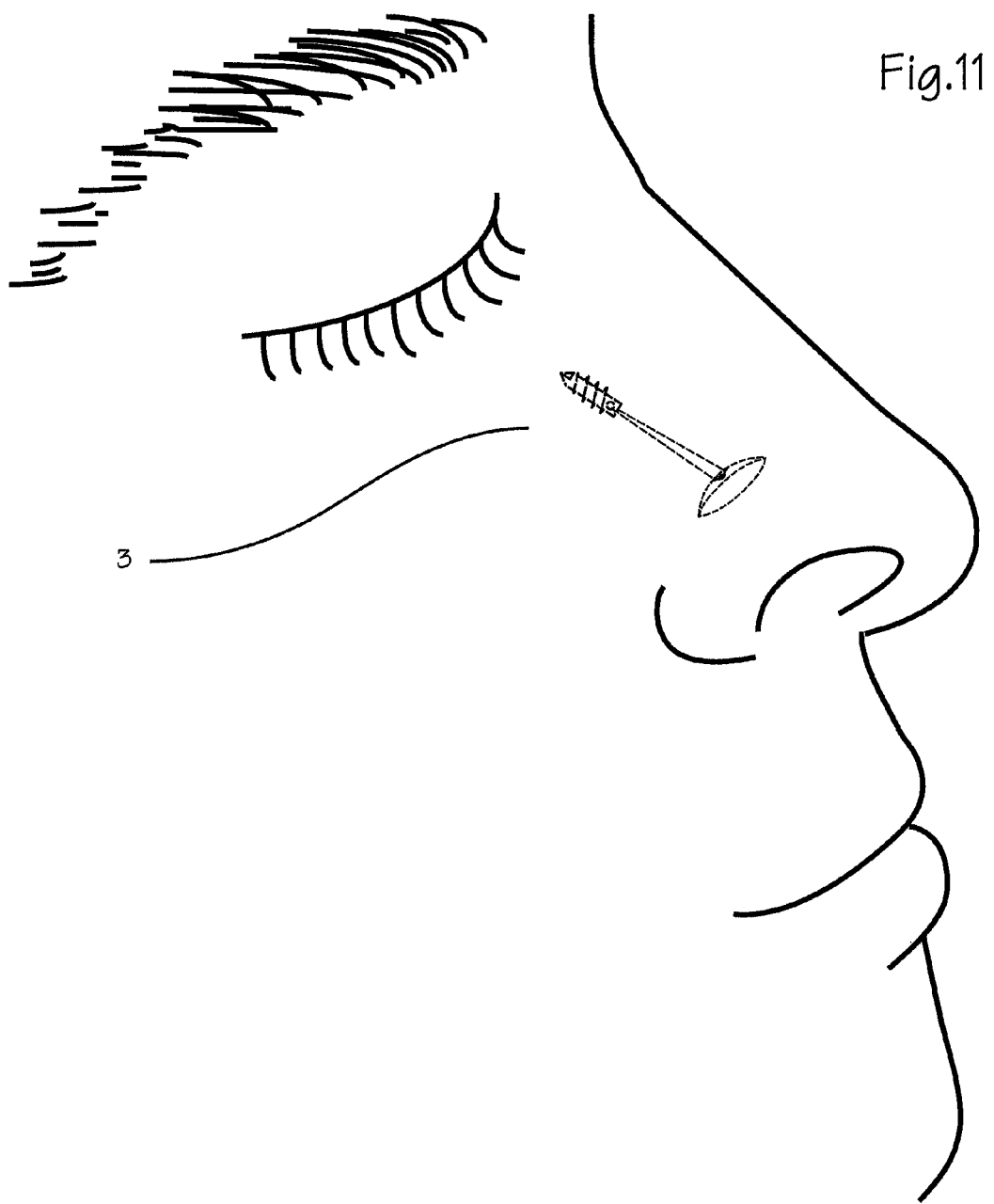

FIG. 8 illustrates that the inserter is disconnected from the suture anchor and the inserter is removed with the trailing suture. A second suture anchor 9 is attached to the distal end of the inserter and the insertion of the second suture anchor is performed similarly to the first suture anchor. The trailing sutures are retrieved via a retriever introduced through the tunnel and pulled through a nasal opening of the patient. FIG. 9 illustrates that the retrieved trailing sutures are fed through holes in the supporter, which has holes for introducing the suture. FIG. 10 illustrates that the supporter is advanced over the suture to place the supporter within the trans-nasal pocket. The supporter is advanced over the sutures and placed within the trans-nasal pocket incision within the tissue of the lateral nasal wall. FIG. 11 illustrates that the tension between the suture anchor, trailing sutures and supporter is created to correct for nasal collapse and maintain open and support the nasal passage of the patient. Upon proper position, the sutures can be tied off and trimmed on the underside of the supporter.

The method may be also performed with insertion of a single suture anchor. The suture anchor 8 is attached to the distal end of the inserter 25 and a trans-nasal puncture of the nasal mucosa near or at the area of collapse is performed. The suture anchor is advanced via the inserter into the facial tissue up to the targeted bone fixation location and the suture is attached to the targeted site in the maxilla bone. The inserter is disconnected from the anchor and removed with the suture trailing and exiting the insertion path. The supporter is advanced over the trailing suture and placed within the trans-nasal pocket incision within the tissue of the lateral nasal wall. The tension between the suture anchor, trailing suture and supporter is created to correct for nasal collapse and maintain open and support the nasal passage of the patient.

The methods are performed such that a transconjuctival or facial incision is avoided in the treatment of nasal valve collapse. The methods also avoid other facial incisions such as the transcolumellar incision used in the external or open rhinoplasty approach. Delivery of the supporter is through the internal nasal wall and adjacent tissues to attach a fixation device using only a trans-nasal or endo-nasal approach.

Alternatively, the method may be performed through an invasive trans-oral and trans-nasal procedure. A first suture anchor is attached to the distal end of the inserter 25 and the inserter is tunneled trans-orally (from a position superior-lateral from the patient's teeth) to a targeted bone fixation location. The anchor suture is attached to the bone and the inserter is disconnected from the suture anchor and removed. A second suture anchor 9 is attached to the distal end of the inserter 25 and introduced into the maxilla bone. A suture retriever is inserted trans-nasally through the lateral nose wall to the suture anchor point and retrieves and pulls the trailing sutures through the nasal opening. A supporter is introduced through the trailing sutures and tensioned to a desired tension to correct for nasal collapse and maintain open and support the nasal passage of the patient. This method may alternatively be performed with a single suture anchor.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A method for maintaining a patient's nasal value to prevent occlusion of the patient's nasal passage comprising:

trans-nasally forming a tunnel to access a patient's nasal mucosa;

driving a first suture anchor having a first trailing suture through the tunnel to create a trans-nasal pocket and implanting the first suture anchor into a targeted location;

inserting a suture retriever through the tunnel to retrieve the first trailing suture and pulling the first trailing suture through a nasal opening of the patient;

driving a second suture anchor having a second trailing suture through the tunnel and implanting the second suture anchor into a second targeted location;

inserting a suture retriever through the tunnel to retrieve the second trailing suture and pulling the second trailing suture through a nasal opening of the patient;

feeding the first and second trailing sutures through a supporter having holes for introducing the trailing sutures and advancing the supporter over the trailing sutures to place the supporter within the trans-nasal pocket of the patient; and tensioning the suture anchors, trailing sutures and supporter to correct for nasal collapse and maintain open the nasal passage of the patient.

2. The method of claim 1 further comprising the step of tying off the trailing sutures and trimming the trailing sutures on the underside of the supporter.

3. The method of claim 1 wherein the step of trans-nasally forming the tunnel is performed by introducing a hypodermic needle with a stylet into the nasal mucosa and then withdrawing the stylet.

4. The method of claim 1 wherein the step of driving the suture anchors is performed by an inserter.

5. The method of claim 1 wherein the target region for placement of the suture anchors is in the patient's maxilla bone.

6. The method of claim 1 wherein tensioning suture anchors, trailing sutures and supporter is performed within the nasal valve tissue of the patient.

7. The method of claim 1 wherein the target region for the supporter is underneath the endonasal mucosa at the internal nasal valve of the patient.

* * * * *